(12) United States Patent
Borza

(10) Patent No.: US 7,574,369 B1
(45) Date of Patent: Aug. 11, 2009

(54) DATA RECORDING, BILLING, CHARGES, AND QUALITY ASSURANCE SOFTWARE FOR MOBILE DEVICES

(75) Inventor: John Michael Borza, Gibsonia, PA (US)

(73) Assignee: Eanesthesia Software LLC, Gibsonia, PA (US)

( * ) Notice: Subject to any disclaimer, the term of this patent is extended or adjusted under 35 U.S.C. 154(b) by 1090 days.

(21) Appl. No.: 10/269,116

(22) Filed: Oct. 10, 2002

Related U.S. Application Data

(60) Provisional application No. 60/328,525, filed on Oct. 11, 2001, provisional application No. 60/386,095, filed on Jun. 4, 2002.

(51) Int. Cl.
- G06Q 10/00 (2006.01)
- G06Q 50/00 (2006.01)
- G06Q 99/00 (2006.01)
- A61B 5/00 (2006.01)
- G06F 19/00 (2006.01)

(52) U.S. Cl. .................................. 705/2; 705/3; 705/52

(58) Field of Classification Search .................. 705/2–3
See application file for complete search history.

(56) References Cited

U.S. PATENT DOCUMENTS

| | | | | |
|---|---|---|---|---|
| 4,857,716 A | * | 8/1989 | Gombrich et al. | 235/375 |
| 4,916,441 A | * | 4/1990 | Gombrich | 345/169 |
| 5,651,775 A | * | 7/1997 | Walker et al. | 604/207 |
| 5,718,223 A | * | 2/1998 | Protas et al. | 128/204.21 |
| 5,867,821 A | * | 2/1999 | Ballantyne et al. | 705/2 |
| 5,955,937 A | * | 9/1999 | Groen | 338/22 SD |
| 5,974,238 A | * | 10/1999 | Chase, Jr. | 709/248 |
| 5,995,937 A | * | 11/1999 | DeBusk et al. | 705/2 |
| 5,999,909 A | * | 12/1999 | Rakshit et al. | 705/2 |
| 5,999,999 A | * | 12/1999 | Homitsu et al. | 710/307 |
| 6,088,677 A | * | 7/2000 | Spurgeon | 705/4 |
| 6,149,440 A | * | 11/2000 | Clark et al. | 434/322 |
| 6,171,112 B1 | * | 1/2001 | Clark et al. | 434/322 |
| 6,314,556 B1 | * | 11/2001 | DeBusk et al. | 717/107 |
| 7,188,151 B2 | * | 3/2007 | Kumar et al. | 709/217 |
| 2003/0065537 A1 | * | 4/2003 | Evans | 705/2 |

OTHER PUBLICATIONS

O'Connor et al., Clinical Skills Training: developing objective assessment instruments, 1997, Blackwell Science Ltd., vol. 31, pp. 359-363.*

* cited by examiner

*Primary Examiner*—Gerald J. O'Connor
*Assistant Examiner*—Amber L Altschul
(74) *Attorney, Agent, or Firm*—Reed Smith LLP

(57) ABSTRACT

A software-based system and method for providing data collection, recording, billing, supply charges, and quality assurance for a mobile computing environment. Specifically, the present invention comprises a plurality of mobile, handheld computer devices to be used in combination with a main computer to facilitate the recording, manipulation, and reporting of data pertaining to a plurality of different patients in a hospital setting. The system includes handheld software that allows an anesthesia provider to log information related to a patient during an anesthesia procedure. A subsequent synchronization step allows that information to be automatically transferred to the main computer for storage and subsequent report generation and printing. The information can also be transferred to an attached or remote computer system (e.g., the hospital or insurance company computer network) for further processing.

28 Claims, 15 Drawing Sheets

| DX | | | AGE | HT | WT | MEDICATIONS |
|---|---|---|---|---|---|---|
| PROPOSED SURGERY | | | | | | RX _____ |

PREOP BP HR RR T O-SAT MENTAL STATUS
VITALS: ALERT___ ORIENTED___ NPO STATUS___

OTHER:

DRUG ALLERGIES

CV:
- ○ HTN_____ ○ MI_____ ○ ANGINA_____ ○ CHF_____
- ○ DYSRHYTHMIA_____ ○ PACER/AICD_____ ○ PVD_____
- ○ PE/DVT_____ ○ OTHER_____

CARDIAC EVAL _____
○ PULMONARY DX _____

PULMONARY
- ○ REACTIVE AIRWAY DX ○ CPAP_____ ○ RECENT URI_____
- ○ ORTHOPNEA_____ ○ ASTHMA_____
- ○ SLEEP APNEA ○ _____ CPAP ○ SMOKER_____

GI/HEPATIC ○ LIVER DX_____ ○ GI DX_____ ○ HH/GERD_____
GU. ○ KIDNEY DYSFUNCTION _____
○ OB PATIENT P G_____ ○ LMP_____ ○ POST MENO

HEME ○ DISORDERS_____ ○ HX BLEEDING PROBS_____
ENDO ○ DIABETES_____ ○ OTHER_____
NEURO ○ CVA_____ ○ OTHER_____
○ SEIZURE_____
○ DEFICITS_____ ○ BACK PAIN/PROBS_____

ORTHO ○ OA/RA_____ ○ OTHER_____
AIRWAY DENTITION_____ ORAL_____ NECK_____
○ TMJ ○ HX DIFFICULT AIRWAY_____

○ OTHER _____ KEY ○=POSITIVE ○=NEGATIVE

PREVIOUS ANESTHETICS ☐ PERSONAL/FAMILY HX PROBS GA/OTHER + −

MEDICATIONS (right column):
OTC/HERBAL _____
ETOH/ILLICITS _____
LAB _____
HGB/HCT _____ WBC _____
PLATELETS _____ BT _____
PT _____ PTT _____ INR _____
NA ___ K ___ CL ___ CO₂ ___
BUN ___ CR ___ BS ___
PREGNANCY TEST _____
OTHER/ABNORMALS _____

EKG _____
CXR _____
OTHER _____

INTERVIEWER _____ DATE _____

ANESTHESIA PLAN
- ☐ CHART REVIEWED
- ☐ PT EXAMINED AND RE-EVALUATED IMMEDIATELY PRIOR TO ANESTHESIA
- ☐ CARE PLAN DISCUSSED

RISKS, BENEFITS AND ALTERNATIVES EXPLAINED QUESTIONS ANSWERED AND PATIENT/RESPONSIBLE PARTY ACCEPTS PLAN FOR ANESTHESIA

ANESTHESIOLOGIST _____ DATE _____

NOTES

ASA  I  II  III  IV  V  E

POST OP NOTES ☐ phase II ☐ PACU ☐ ICU
VITALS BP
HR
RR
O2 SAT
COMMENT

ADDITIONAL COMMENTS (Inpatient follow up/other)

TIME ___ DATE ___ ANESTHESIOLOGIST ___ | TIME ___ DATE ___ ANESTHESIOLOGIST ___

ANESTHESIA/NURSING PREOPERATIVE ASSESSMENT

Figure 2

PHYSICIAN'S ORDERS
ANESTHESIA DRUG CHARGES

| ORDERS AND SIGNATURES | | | | | | |
|---|---|---|---|---|---|---|
| ALBMDI | ____ | Albuterol Inhaler PROVENTAL/VENTOLIN | 17gm | MUSCLE RELAXANTS | | |
| TEAROSUD | ____ | Artificial Tears Oph Soln PF 0.6ml | 0.6ml | ATRC50I ____ Atracurium 10mg/ml | | 5ml |
| ATR1I | ____ | Atropine Injection 1mg | 1ml | PAN2I ____ Pancuronium 2mg/ml PAVULON | | 5ml |
| ATR1J | ____ | Atropine Syringe 1mg/10ml | 10ml | RAPLON ____ Rapacuronium 20mg/ml RAPLON | | 5ml |
| CACLJ | ____ | Calcium Chloride 10% 1gm/10ml syringe | 10ml | ROC50I ____ Rocuronium Inj 10mg/ml ZEMURON | | 5ml |
| DEX4I | ____ | Dexamethasone Inj 4mg/ml DECADRON | 1ml | SUCC200I ____ Succinylcholine 20mg/ml ANECTINE/QUELICIN | | 10ml |
| DEX20I | ____ | Dexamethasone Inj 4mg/ml DECADRON | 5ml | TUB30I ____ Tubocurarine 3mg/ml/CURARE | | 10ml |
| D50W50J | ____ | Dextrose Syringe 50%/25gm | 50ml | | | |
| DIP50I | ____ | Diphenhydramine Inj 50mg/ml BENADRYL | 1ml | LOCAL ANESTHETIC AGENTS | | |
| DOXPI | ____ | Doxaprom Inj 20mg/ml DOPRAM | 20ml | ____ Bupivacaine/MARCAINE/SENSORCAINE ___%___ | | ml |
| DROP5I | ____ | Droperidol 2.5mg/ml INAPSINE | 2ml | w/EPINEPHRINE _____%_____ | | ml |
| EDR10I | ____ | Edrophonium 10mg/ml TENSILON | 1ml | BUPD752 ____ Bupivacaine 0.75% Dex SPINAL MARCAINE | | 2ml |
| EPH50I | ____ | Ephedrine Sulfate Inj 50mg/ml | 1ml | LID550PF ____ Lidocaine 0.5% Inj. Preservative Free | | 50ml |
| EPI1J | ____ | Epinephrine Syringe 1mg/10ml SHORT ADRENALIN | 10ml | LID550 ____ Lidocaine 0.5% Inj. | | 50ml |
| | | | | LIDE550 ____ Lidocaine 0.5% w/EP 1:200,000 | | 50ml |
| EPI1CJ | ____ | Epinephrine Syringe 1mg/10ml CARDIAC ADRENALIN | 10ml | LID12 ____ Lidocaine 1% Inj | | 2ml |
| | | | | LID120 ____ Lidocaine 1% 20ml | | 20ml |
| EPI1PF | ____ | Epinephrine Inj 1mg/ml ADRENALIN | 1ml | LIDE120 ____ Lidocaine 1% w/EPI 1:100,000 | | 20ml |
| ESM100I | ____ | Esmolol Inj 10mg/ml BREVIBLOC | 10ml | LID1520PF ____ Lidocaine 1.5% Inj PF | | 20ml |
| ETOJ20 | ____ | Etomidate 2mg/ml AMIDATE | 10ml | LID220 ____ Lidocaine 2% Inj. 20ml | | 20ml |
| FLUM5I | ____ | Flumazenil 0.1mg/ml ROMAZICON | 5ml | LIDJEL5 ____ Lidocaine 2% Jelly | | 5ml |
| FUR20I | ____ | Furosemide 20mg/2ml LASIX | 2ml | LIDE220 ____ Lidocaine 2% w/EPI 1:100,000 | | 20ml |
| GLYC2I | ____ | Glycopyrrolate Inj 0.2mg/ml ROBINUL | 1ml | LID5D75 ____ Lidocaine 5% & Dextrose 7.5% SPINAL | | 2ml |
| HEP1KUD | ____ | Heparin Inj 1000u/ml | 10ml | ____ Mepivacaine/POLOCAINE _____%_____ | | ml |
| HEP100 | ____ | Heparin Lock Flush 100u/ml | 10ml | TETC1I ____ Tetracaine Inj 1% PONTOCAINE | | 2ml |
| HET500 | ____ | Hetastarch 6% in NS HESPAN | 500ml | | | |
| HYDC100I | ____ | Hydrocortisone 100mg/2ml SOLU-CORTEF | 2ml | INHALATION ANESTHETIC AGENTS | | |
| HYDC250I | ____ | Hydrocortisone 250mg/2ml SOLU-CORTEF | 2ml | DESFIN ____ Desflurane Unit x___ used SUPRANE 1 hour=1 unit | | |
| INSHR | ____ | Insulin, Human Regular 100unit/ml | 10ml | ISOFIN ____ Isoflurane Unit x___ used FORANE 1 hour=1 unit | | |
| KET60I | ____ | Ketorolac Inj 30mg/ml TORADOL | 2ml | SEVIN ____ Sevoflurane Unit x___ used ULTANE 1 hour=1 unit | | |
| LABI | ____ | Labetalol Inj 5mg/ml NORMODYNE | 20ml | | | |
| LID100J | ____ | Lidocaine 100mg/5ml Syringe | 5ml | CONTROLLED DRUGS | | |
| MINO10 | ____ | Mineral Oil - Light, Sterile | 10ml | Fentanyl 0.05mg/ml SUBLIMAZE ____2ml ____5ml | | |
| MIV20I | ____ | Mivacurium 2mg/ml MIVACRON | 10ml | KETA50I ____ Ketamine 50mg/ml KETALAR | | 10ml |
| NAL4I | ____ | Naloxone 0.4mg/ml NARCAN | 1ml | KETA100I ____ Ketamine 100mg/ml KETALAR | | 5ml |
| NEOS5I | ____ | Neostigmine 1:2000 (0.5mg/ml) PROSTIGMINE | 10ml | MID5I ____ Midazolam 5mg/ml VERSED | | 1ml |
| OPHO | ____ | Opthalmic Lub Ointment/LACRILUBE | 0.7gm | MOR51PF ____ Morphine Sulfate PF 0.5mg/10ml DURAMORPH | | 10ml |
| OND4I | ____ | Ondansetron Inj 2mg/ml ZOFRAN | 2ml | Sufentanil/SUFENTA 0.05mg/ml _____2ml _____5ml | | |
| OXYT10I | ____ | Oxytocin Inj 10unit/ml PITOCIN | 1ml | Other Medications | | |
| PHEE10I | ____ | Phenylephrine Inj 10mg/ml NEOSYNEPHRINE | 1ml | _____ | | |
| POVO | ____ | Povidone Iodine Ointment BETADINE | 1gm | _____ | | |
| PROF2I | ____ | Propofol Inj 10mg/ml DIPRIVAN | 20ml | _____ | | |
| PROF5I | ____ | Propofol Inj 10mg/ml DIPRIVAN | 50ml | _____ | | |
| PROT50I | ____ | Protamine Sulfate 10mg/ml | 5ml | _____ | | |
| PYRS10I | ____ | Pyridostigmine Inj 5mg/ml REGONOL | 2ml | _____ | | |
| NABI10J | ____ | Sodium Bicarb Syringe 10mEq (Pediatric) | 10ml | _____ | | |
| NABI50J | ____ | Sodium Bicarb Syringe 50mEq (Adult) | 50ml | _____ | | |
| NABI50I | ____ | Sodium Bicarb 50mEq Vial | 50ml | _____ | | |
| NSKCL20 | ____ | Sodium Chloride 0.9% 1000ml-KCL20meq | 20mEq | _____ | | |
| NSKCL40 | ____ | Sodium Chloride 0.9% 1000ml-KCL40meq | 40mEq | _____ | | |
| THIP500I | ____ | Thiopental Syringe 2.5% 25mg/ml PENTOTHAL | 20ml | _____ | | |
| THIP500J | ____ | Thiopental 2.5% 25mg/ml PENTOTHAL KIT | 20ml | _____ | | |

CHECK APPROPRIATE ORDERS IN (✓) COLUMN

Date _____ Time _____ Physician's Signature _____

ANESTHESIA DRUG CHARGES

671-09-115 REV 11/01 SRC

Anesthesia Charge Sheet

[ ]   Penn Campus                              [ ]   Greenlawn Campus

Instructions:   Please check appropriate campus location of surgical/anesthesia procedure, stamp patient's name in upper right hand corner and complete information as required Distribution:   Billing Department, Surgery Department, Date of Service:_____ Surgeon:_____

Procedure:_____

Anesthesiologist:_____ CRNA:_____

Number of Concurrent Cases:_____ Pt Diagnosis _____

Case Start Time:_____          Case Finish Time:_____

Labor Starts:_____             Labor Finish:_____

Delivery Start:_____           Delivery Finish:_____

Other:
_____ Epidural
_____ Swan
_____ A-Line
_____ CVP Line
_____ Pain Management
_____ Misc

DATA RECORDING, BILLING, CHARGES, AND QUALITY ASSURANCE SOFTWARE FOR MOBILE DEVICES

CLAIM OF PRIORITY

This application claims priority to U.S. Provisional Patent Application Ser. No. 60/328,525 filed on Oct. 11, 2001 and U.S. Provisional Patent Application Ser. No. 60/386,095 filed on Jun. 4, 2002.

BACKGROUND OF THE INVENTION

1. Field of the Invention

The present invention relates to software-based systems and methods for providing data collection, recording, billing, supply charges, and quality assurance for a mobile computing environment, and, more particularly, the present invention relates to a mobile computer hardware and software system for the management of multiple patients by multiple medical personnel, especially for anesthesia applications.

2. Description of the Background

In many diverse environments, a large amount of data must be gathered and recorded for future use by one or more personnel related to the information thus gathered. Often times, data is gathered on multiple subjects at various recurring times in order to track changes that occur and determine whether to change the management of each particular subject. Management of these vast amounts of data, especially where the data for each subject must be kept isolated from other data, can be an onerous project. Historically, these data management systems constituted voluminous paper records and a complex web of sub-systems allowing for various subsequent tasks and records to be produced.

The medical field has countless examples of procedures in which data for many different patients must be collected over an extended period of time. For example, common today is the practice of making handwritten anesthesia records, handwritten pharmacy drug charge forms, handwritten quality assurance forms, handwritten supply charges (e.g., masks, tubing, syringes and other general hospital supplies), and handwritten anesthesia billing forms. Several of these handwritten papers are shown in the figures: FIG. 1 is an exemplary anesthesia record; FIG. 2 is an exemplary preoperative assessment form; FIG. 3 is an exemplary drug charge form; and FIG. 4 is an exemplary anesthesia charge sheet.

Such a practice is susceptible to mistakes particularly by not documenting appropriate information in view of a busy operating/procedure room environment. By not documenting appropriate information, insufficient information is recorded on the anesthesia record. If thereafter called upon by a medical or legal representative to review what occurred with a particular patient, there may be nothing recorded to verify care given. Further, because the operating/procedure room environment is extremely busy, anesthesia providers don't readily document pharmacy drug charges or supply charges, which results in lost revenue for the hospital. Again, with the hectic nature of the operating/procedure room environment, documenting appropriate surgical procedures along with anesthesia start/stop times is historically inaccurate.

By having to rely on handwritten documentation, time is wasted that could otherwise be used to direct and provide needed care to the patient. Further, since there is only one copy of the multiple different forms created, losing just one particular form would have a significant negative impact on documentation, billing, drug charges, supply charges, or altering the results of quality assurance. By losing the anesthesia record, you have no documentation of what happened and what kind of care was provided. By losing the billing form, supply charges form, or pharmacy drug charge form, you are dealing with lost revenue, and by losing the quality assurance form, you are not creating accurate results of the evaluation of care provided. A single system for automatically maintaining, creating, and storing the information from these various forms is desired and has been partially addressed through prior practices.

Traditionally, computer applications have been written in an attempt to solve the problems of anesthesia recording, but have met with limited success. Utilizing a software application on a standard personal computer (PC) not only brought limited benefits, but created additional problems as well. For example, the PC is stationary, bulky, and takes up space that is already limited in the operating/procedure room. In these prior systems, the health care professional still needs to gather initial information on paper and then enter that information into the computer. The PC is typically fixed behind the anesthesia provider, such that the anesthesia provider is not monitoring the patient, which means that the patient is not receiving the full attention of the anesthesia provider.

The prior art anesthesia applications may be complicated and not straightforward to use, often requiring classes or other extensive training in order to use the application. This may create additional problems when a locum tenens anesthesia provider, who is usually not given any orientation, is providing care. Also, because the application is typically set up such that data is automatically pulled from the patient monitors, errors can result on the anesthesia record due to a variety of circumstances. For example, this may occur when the surgeon is using an electrical cauterizing device, which interferes with the PC system, which in turn causes the PC to document spurious or incorrect data.

These prior art systems are also limited because the data cannot be edited. If a problem occurs and the data needs to be examined, the anesthesia professional is therefore in the awkward position of defending a document that was intended to defend the user. Typically, at the end of the procedure, the anesthesia record must be printed out before leaving the operating/procedure room. In the prior systems, this causes an additional delay that is not in the best interests of the patient who now must wait for the printing before being taken to the post anesthesia care unit for recovery. Therefore, incomplete information may be quickly printed, information may be left out of the report entirely, or information may be hand-appended at a later time. Each of these "fixes" limits the utility of the prior computer-based systems and does not adequately address the problems with paper-based systems.

As such, an integrated system that allows for the intuitive and automatic collection of data that also allows for automatic quality assurance processing and printing of reports, supply charges, and bills is desired. Such a system may be used in a wide variety of applications in which a large range of data is periodically collected from multiple subjects. The invention may be especially useful in the medical arts—such as anesthesiology. The present invention, in at least one preferred embodiment, addresses one or more of the above-described and other limitations to prior art systems.

SUMMARY OF THE INVENTION

In accordance with at least one preferred embodiment, the present invention provides data recording, billing, charges, and quality assurance software for mobile devices. Specifically, the present invention comprises a plurality of mobile, handheld devices to be used in combination with a main computer to facilitate the recording, manipulation, and reporting of data pertaining to a plurality of different patients in a surgical/procedure (e.g., hospital, surgery center, or office) setting.

In at least one preferred application, the present invention includes handheld software that allows an anesthesia provider to log information related to a patient during an anesthesia procedure. A subsequent synchronization step allows that information to be automatically transferred to the main computer for storage. Thereafter, this stored information can be used to print reports or can be transferred to an attached or remote computer system (e.g., the hospital, anesthesia office of business, or insurance company computer network) for further processing.

In some embodiments, the present invention has many advantages that will benefit the healthcare professional and patient in relation to prior systems. For example, the present system saves time and reduces paperwork which lower the cost of health care. The system eliminates lost drug and supply charges and makes reporting more uniform. The system further makes sure that all preliminary disclosures are made to patients and their families and that proper procedures are documented. Such activities ensure patient success.

BRIEF DESCRIPTION OF THE DRAWINGS

For the present invention to be clearly understood and readily practiced, the invention will be described in conjunction with the following figures, wherein like reference characters designate the same or similar elements, which figures are incorporated into and constitute a part of the specification, wherein:

FIG. 2 shows an exemplary paper-based preoperative assessment record;

FIG. 3 shows an exemplary paper-based drug charges record;

FIG. 4 shows an exemplary paper-based anesthesia charge sheet;

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. Those of ordinary skill in the art will recognize that other elements are desirable and/or required in order to implement the present invention. However, because such elements are well known in the art, and because they do not facilitate a better understanding of the present invention, a discussion of such elements is not provided herein. The detailed description will be provided hereinbelow with reference to the attached drawings.

The present invention provides, in at least one preferred embodiment, a hardware and software system that greatly enhances the accuracy, quality and speed of the acquisition and reporting of data used for various types of record-keeping. Although the invention may be used across a wide variety of technical applications, it may be particularly useful in the medical field, as much data about many different patients must be simultaneously and accurately recorded to thereafter generate accurate charts and records. Although the present application and system may be used in many different applications, the anesthesia area is a particularly apt use, and will be used by way of example throughout this specification. Although anesthesia is used, the scope of this detailed description and the appended claims should not, in any way, be limited to this specific application, except as otherwise noted.

In at least one preferred embodiment, the present invention comprises a software application that creates an anesthesia record, a pharmacy drug charge form, an anesthesia billing form, supply charge form, and a quality assurance database query, all from information entered into a handheld device by an anesthesia provider. The software on the handheld device facilitates quick and accurate decision-making and recording of pertinent information, and it ensures that proper disclosures and levels of quality are maintained. The information in the handheld device is later synchronized to a main computer for subsequent storage, printing, and transmission to additional computer systems.

Figure 1:
FIG. 1 shows an exemplary paper-based anesthesia record.
Figure 5:
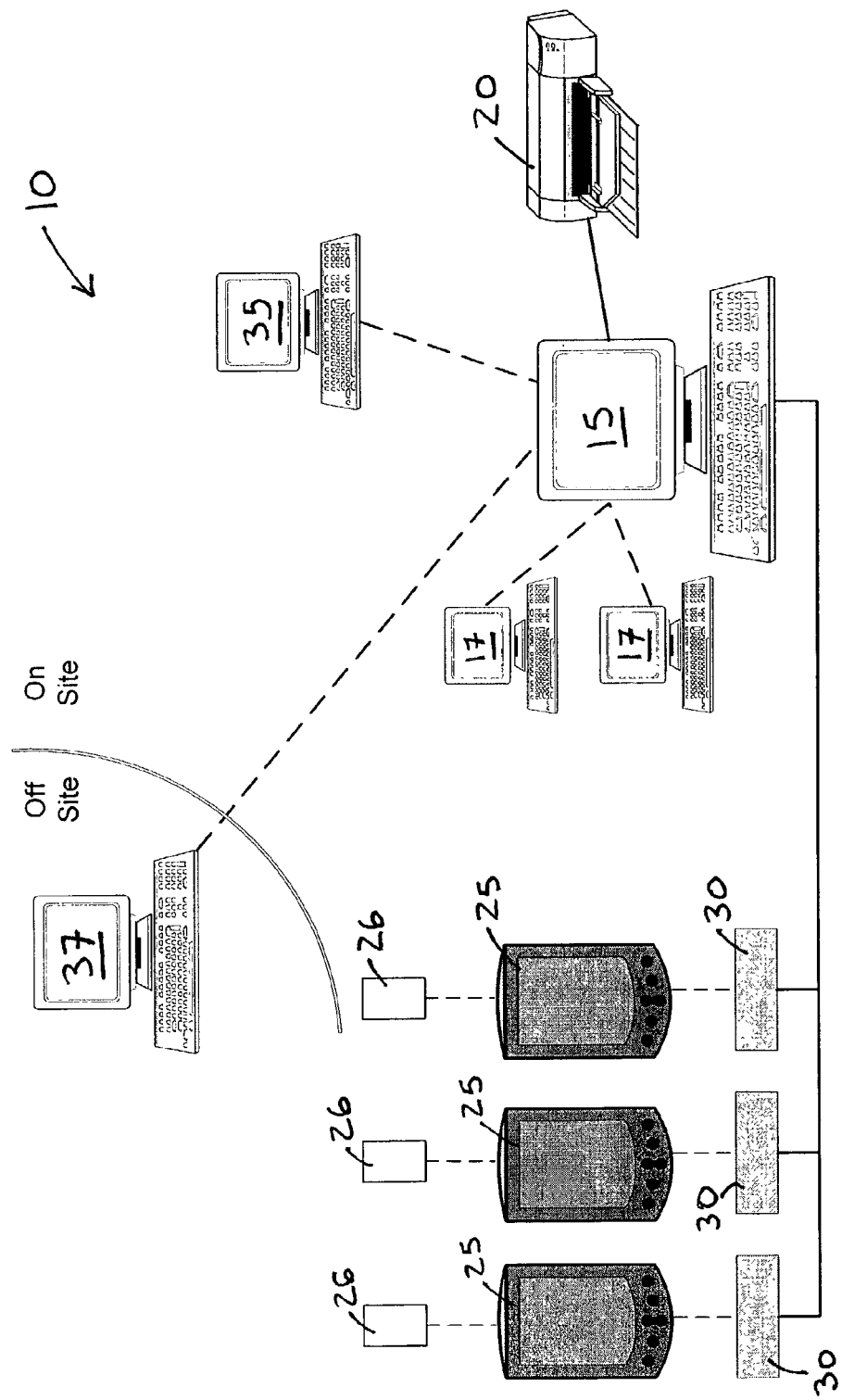
FIG. 5 is a system block diagram of the major hardware and software components of the data management system.

FIG. 5 provides a general system overview of the major hardware and software components that make up the present data management system. The main components of the system 10 comprise: a main computer 15 which may be a server, terminal or a personal computer (PC); a printer 20; and one or more handheld computers 25 with the ability to transfer patient data and other information to and from the main computer 15. In order to transfer the information from the handheld computer 25 and vice versa, the system 10 preferably utilizes a special docking cradle 30, such as a "HOTSYNC" cradle for use with the PALM series of handheld portable computing devices. The synchronization process automatically exchanges and updates data between the one or more handheld devices 25 and the main computer 15. The synchronization process preferably necessitates only the placement of the handheld device 25 on the cradle 30 and the activation of a button or other indicator on the cradle. At this point, the synchronization process will automatically transfer the pertinent information to the main computer 15, and a message will be sent to the handheld device 25 indicating when the transfer is complete.

More specifically, as seen in FIG. 5, a hospital may include a main computer 15 or other computers 17 that are hooked together via a network, shared disk drive or other communications medium. This main computer 15 stores the main components of the software system and the databases that store all of the patient information that is collected and managed by the system 10. The main computer 15 preferably also includes the functionality to generate the various reports (e.g., anesthesia record, preoperative assessment, drug charges, supply charges, and anesthesia charge sheet, similar to those shown in FIGS. 1-4) that facilitate quick and accurate patient administration functions. The main computer 15 is preferably connected to one or more printers 20 (either by cable or wireless link) that allow for the printing of these various reports.

The main computer 15 may also be connected to the hospital computer local area network (LAN) 35 or other communications medium to facilitate data transfer between the one or more handheld computers 25 and the hospital computer system 35. For example, in order to properly bill the patient for a particular drug used during the anesthesia operation, the main computer 15 preferably communicates this information to the hospital pharmacy department computer 35 on a periodic or user-directed basis. This internal data transfer operation preferably increases the likelihood that the hospital correctly bills the patient for all of the care given during the patient's stay in the hospital.

The main computer 15 is preferably connected to one or more handheld device cradles 30 which facilitate communication between the one or more handheld devices 25 and the main computer 15. Specifically, after one of the handheld devices 25 is taken to the operating/procedure room during the administration of anesthesia to a patient (as an example of system use), the anesthesia provider preferably returns the handheld device to a cradle 30 connected to the main computer. Once cradled, the anesthesia provider preferably begins the synchronization process by pressing a button on the cradle 30. During the synchronization process, all of the data collected during the administration of the anesthesia is downloaded ("synched") to the main computer software application. The information about each specific patient is preferably stored separately in the main computer 15, or in an attached or networked database. The information may be printed via an attached or networked printer 20. As indicated above, this information may also be communicated to the various departments attached to the hospital computer network 35, or even to an external computer 37 (e.g., an insurance provider's computer). The possibilities are almost limitless.

After the synching operation, the handheld device 25 is ready to be used by the same or a different anesthesia provider to begin another anesthesia procedure on the same or another patient. In this way, an incoming anesthesia provider may select any of the available handheld devices 25 that are currently in a respective cradle 30 (preferably charging the battery of the handheld device).

When the new anesthesia provider selects a handheld device 25 to be used during a procedure, the provider needs to determine whether the patient has already been created on the system 10. If the patient already exists in the system database, then the anesthesia provider preferably selects this patient from a list of available patients and downloads the previous general patient information to the handheld device 25. Once downloaded, the anesthesia provider is ready to move to the procedure room and begin administration of the anesthesia. If the patient is a new patient, the anesthesia provider preferably inputs some initial general patient information into the software running on the mobile handheld device 25 to initialize the new patient.

Whether for a new or existing patient, the anesthesia provider preferably utilizes the handheld device 25 during the procedure to monitor patient vital statistics, drug administration, and other important information as described more fully below. The various statistical information (i.e., anesthesia patient information) may be entered into the handheld device 25 by the anesthesia provider using a stylus, or the information may be directly sent from a hospital monitor to the handheld device 25 via a wired or wireless data connection. If the anesthesia providers are switched during the procedure, the device merely needs to be handed off to the subsequent provider. Alternatively, the new anesthesia provider may simply swap the back-up data card 26 in the handheld with the previous provider.

This "swaps" the patient information, but care must be taken to delete the patient information from the original handheld device to prevent spurious data. Once the procedure is completed, the handheld device 25 may be placed back on the cradle 30 and a synchronization operation may then be undertaken as described above.

More than one procedure may preferably be undertaken at the same time. The software running on the main computer 15 preferably tracks which patients have been "checked out" of the system, and will not let two handheld devices 25 check out the same patient at the same time (which may cause data loss or overlap). The system is expandable to any number of main computers 15 and databases, as well as any number of handheld devices 25. Different devices may be used for different types of procedures, and different functionality may be imparted to different devices.

The above description detailed the major components and interaction of these components during use of the system. Below, the detailed operation of the system will be described using the example of the software used by an anesthesia provider. This description is offered by way of example only, and should not be used to limit the scope of the appended claims. For the purposes of this description, the initial patient information that is generally biographical and is downloaded from the main computer or entered directly into the handheld device is referred to as "general patient information" and the data pertaining to the anesthesia procedure that is collected and entered into the handheld device is referred to as "anesthesia patient information".

According to the present invention, an anesthesia provider uses a handheld computer to record the collected information about a patent necessary to provide anesthesia care. For security and privacy of patient information, the handheld device preferably offers a security feature. For example, the anesthesia provider may be required to enter a preset password on the opening screen of the handheld to unlock the handheld.

Figure 6:
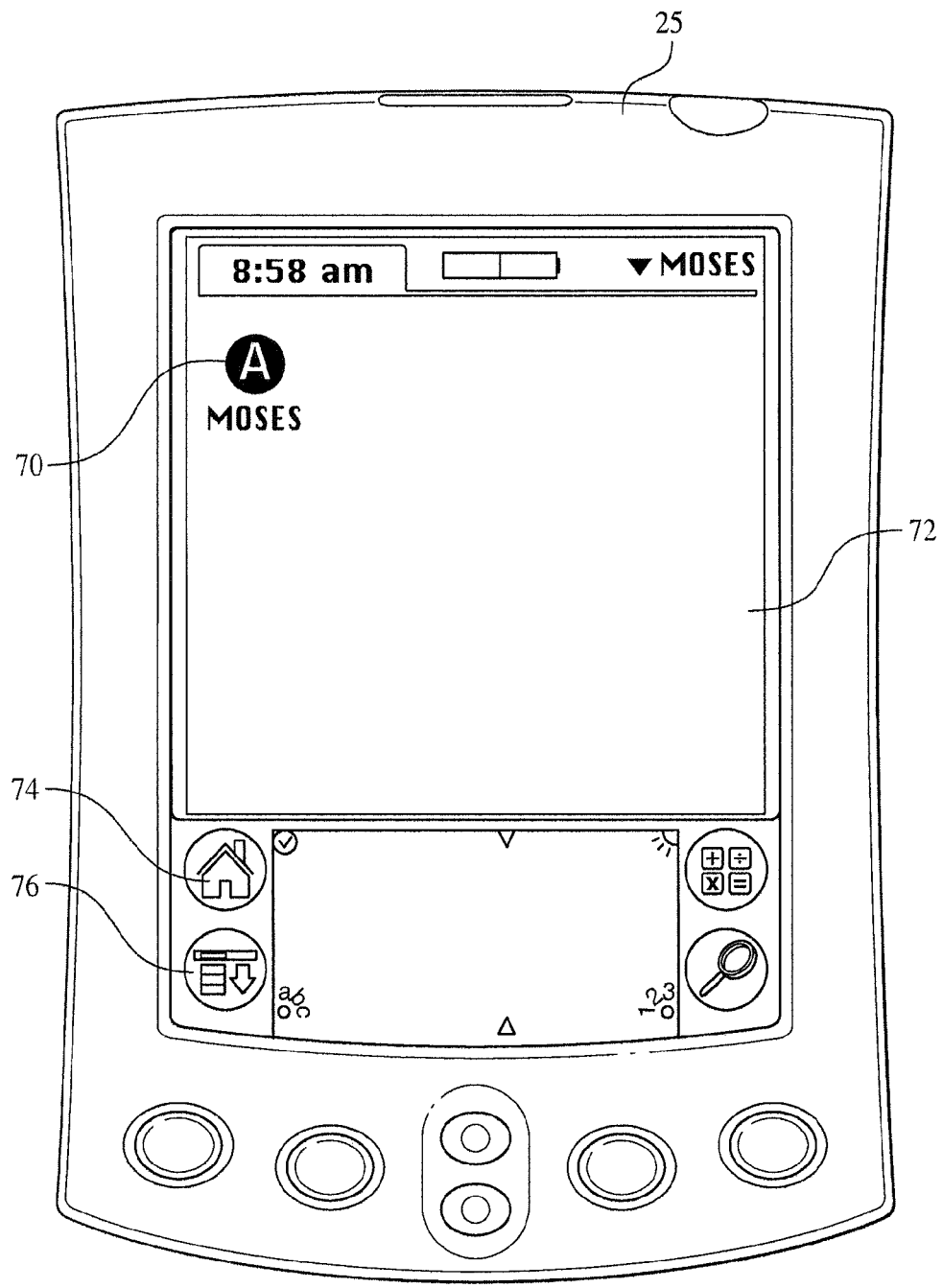
FIG. 6 is a screen capture of an exemplary program introductory screen.

The system is now ready to acquire data from patient interviews and other sources of information. When the anesthesia provider needs to start the application, an appropriate computer icon on the screen may be selected. FIG. 6 shows an exemplary handheld device 25 (in this case a PALM M515) with a program icon 70 depicted thereon.

The handheld device 25 includes a program 72 area in which the handheld data acquisition program may be displayed and in which the user may use a stylus to "tap" and select various selectable choices and enter information. The handheld device 25 also preferably includes a "home" selection area 74 to return to the program selection screen, and a "menu" selection area 76 that can be used within the program to bring up a series of drop-down menus that facilitate moving throughout the various pages of the program. The specific selections within the menu selection area will be discussed below.

Figure 7:
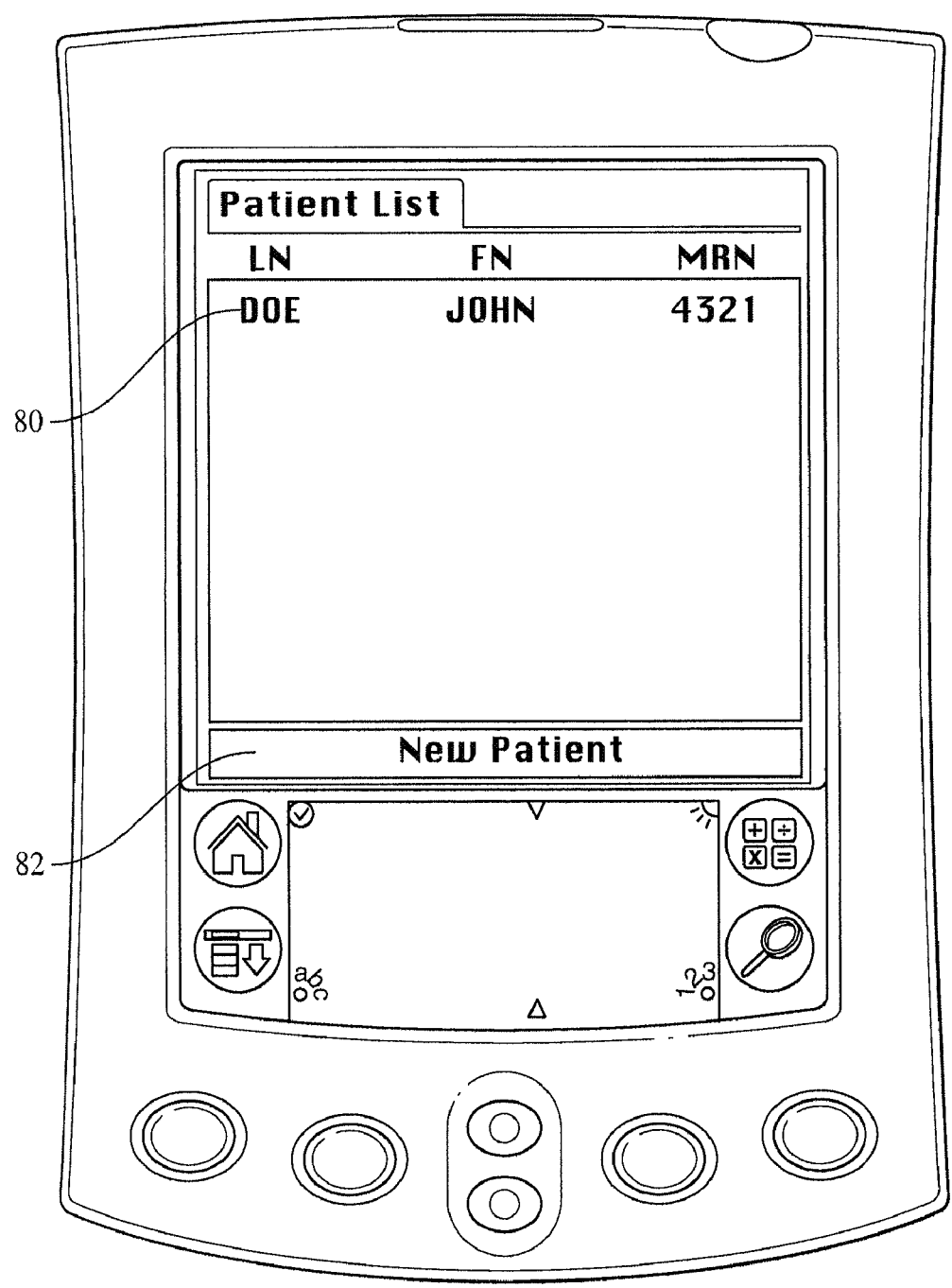
FIG. 7 is a screen capture of an exemplary program patient list screen.
Figure 8:
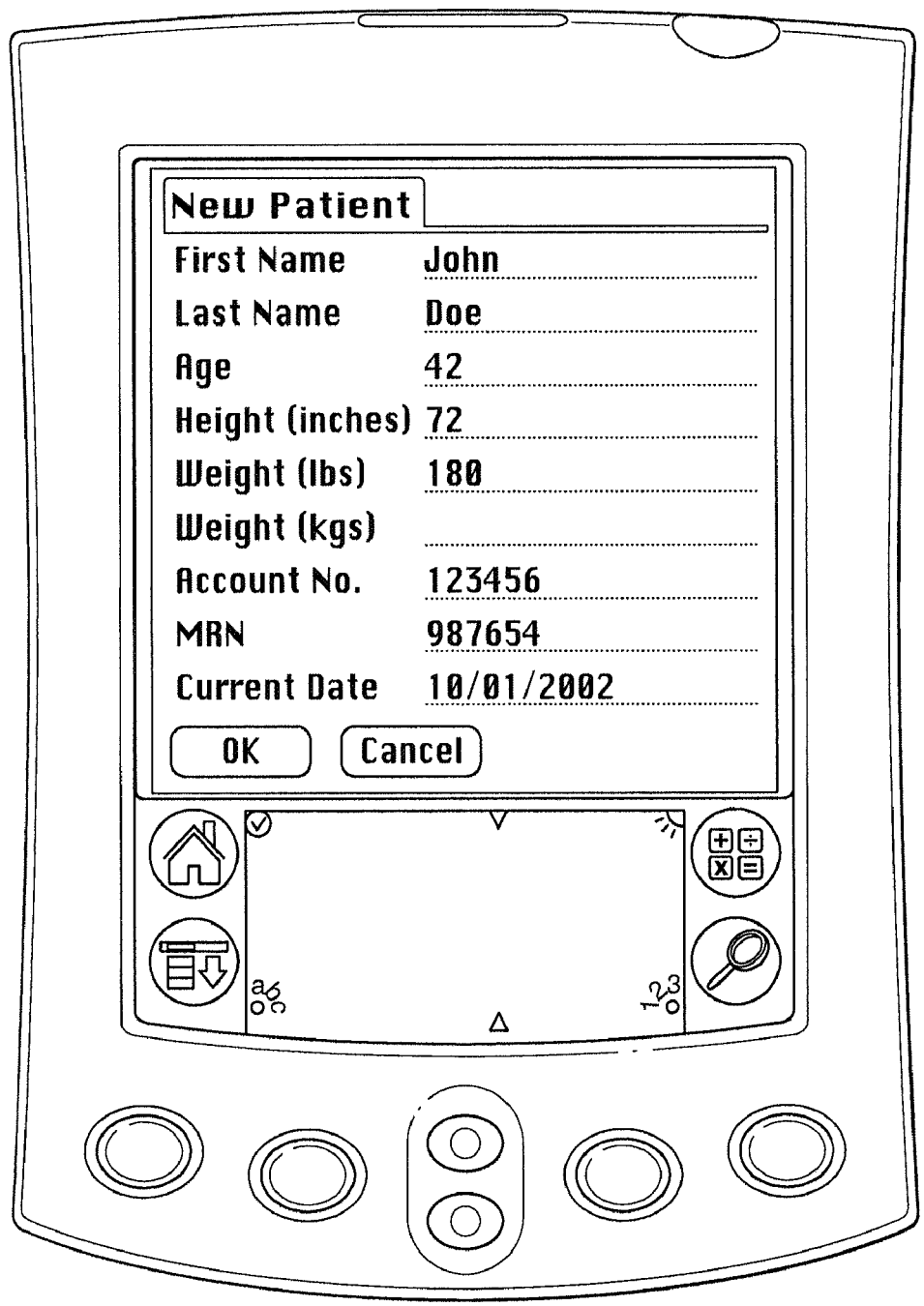
FIG. 8 is an exemplary New Patient Information screen.

After selecting the program icon 70 from the program selection screen, the anesthesia provider is preferably presented with a "Patient List" screen (see, FIG. 7). As shown in FIG. 7, there is a list of previously interviewed patients 80 and a "New Patient" selection area 82 that allows the anesthesia provider to enter information about a new patient. As shown in FIG. 8, when selecting to enter a new patient, the anesthesia provider preferably is prompted to enter general introductory information about the patient being interviewed (e.g., name, age, height, weight, account no., MRN, and current date). When completed, the anesthesia provider taps "OK" (or "cancel" to add a different new patient). Preferably, the anesthesia provider can not proceed further unless the provider verifies through the use of an additional screen that the information about the patient is correct. This verification step is used because the basic patient information (e.g., name, account no., and MRN) generally can not be changed once the patient is created.

Figure 9:
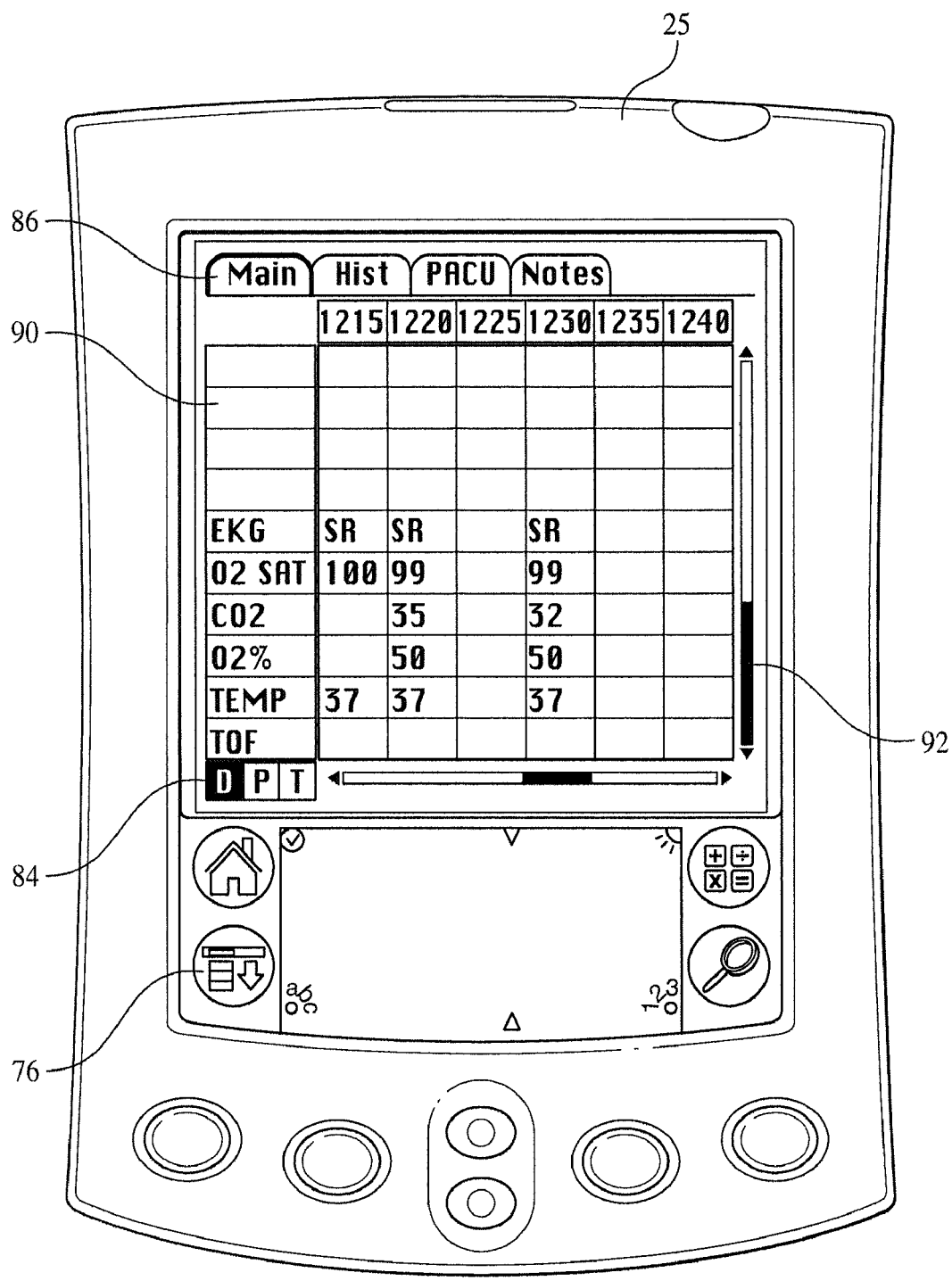
FIG. 9 is an exemplary Dosage Grid screen.

After the appropriate patient is either selected 80 or created 82, the first program screen to appear will be the "Dosage Grid" screen, an example of which is shown as FIG. 9. This screen illustrates the many easy ways in which an anesthesia provider can navigate throughout the program screens. Because so much varied information must be gathered, this easy navigation is important. For example, the major data collection screens include "one-tap" links 84 to the dosage grid ("D"), the blood pressure grid ("P"), and the time screen ("T"). Each of these screens can be immediately accessed by selecting the small letter (D, P, or T) in the lower left-hand corner of the screen. Also, additional sections of the program can be accessed by the selection areas 86 at the top of the program screen (e.g., "Hist" for patient history screens, "PACU" for post anesthesia care unit, and "Notes" for the note screens). Finally, the menu selection area 76 of the handheld device 25 preferably brings up a drop-down menu of navigation features such as a direct link to the major display pages of the program (e.g., Dosage Grid, Blood Pressure Grid, Intubation and Checklist, Times, Signature, Quality Assurance, and Pre-Induction Assessment), each of which will be described in more detail below.

Figure 10:
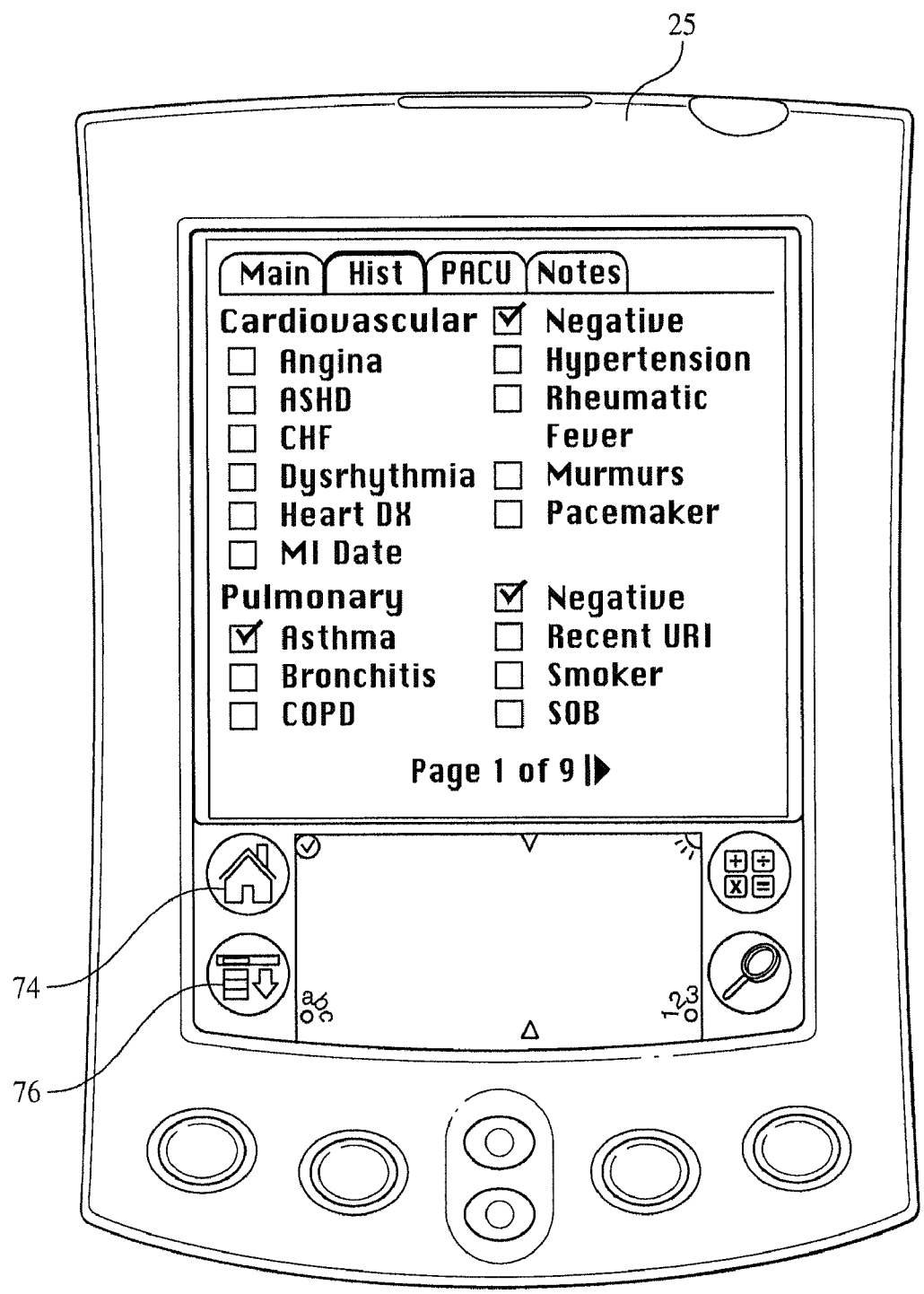
FIG. 10 is an exemplary History screen.

Typically, the anesthesia provider begins a procedure session by interviewing the patient to get background information about the patient's medical and anesthesia history. By selecting the "Hist" tab on top of the screen 86, the anesthesia provider will go to the History section of the application (see, FIG. 10). The History section includes multiple pages of medical history questions with selectable answers (e.g., radio buttons). These questions typically minimize the risk of an adverse patient reaction to the planned course of treatment. For example, the History section preferably includes questions related to the patient's history of: Cardiovascular; Pulmonary; GI-Hepatic; GU-Gyn; Neurology; Allergies; Medications; Laboratory-Chemistry; Laboratory-Hematology; Coag Studies; CXR; ECG; and Anesthesia History. These areas can all be inquired about as necessary for a given procedure, and the list is intended to make sure that a complete history is developed before a patient is anesthetized.

To complete the History section, the anesthesia provider preferably need only check off the appropriate squares (radio buttons) that pertain to the patient that is being assessed. If a box is incorrectly checked, the provider need only tap again to erase the check mark. Further, the system includes drop-down lists to decrease the time and effort expended in writing. Finally, when the anesthesia provider taps a line in which to write information, the appropriate keyboard, either numeric or alphabetic, will preferably pop up on the handheld device screen to ease the effort of entering information.

At any time during the procedure, the anesthesia provider may select the "Home" icon 74 on the handheld 25 to exit out of the application or tap the "Menu" icon 76 on the handheld to choose "New Patient" in order to start a new patient record. Further, the anesthesia provider can tap the Menu icon 76 and select "Display" in order to directly access some of the most often used screens in the program, as described above.

After the History section is filled out, the anesthesia provider typically completes some of the "Notes" pages which can be selected by tapping the "Notes" tab in the Dosage Grid or other screen. Typically, the Notes pages include various information that describes both the location and personnel administering the anesthesia, as well as information directly related to the administration of the anesthesia itself. Often, the information requested as part of the Notes section can be split into that information which should be completed before anesthetizing the patient, and that information which can wait until during or after the procedure. Preferably, at this pre-anesthesia stage of the procedure, the anesthesia provider will input information related to: Anesthesia Care Plan (e.g., general, mask induct., pre-oxygenation, etc.); Regional (e.g., auxiliary block, Bier block, epidural, MAC, etc.); Monitors (e.g., NIBP, EKG, Foley, etc.); Invasive Monitors (e.g., arterial line, CVP, lumen swan ganz, or none); Intubation (e.g., awake, oral, nasal, or none); Post-Anesthesia Care Plan; Analgesia; and Physical Exam. The other information in the Notes page does not necessarily affect the plan for administering the anesthesia and may be completed later, as described below.

Figure 11:
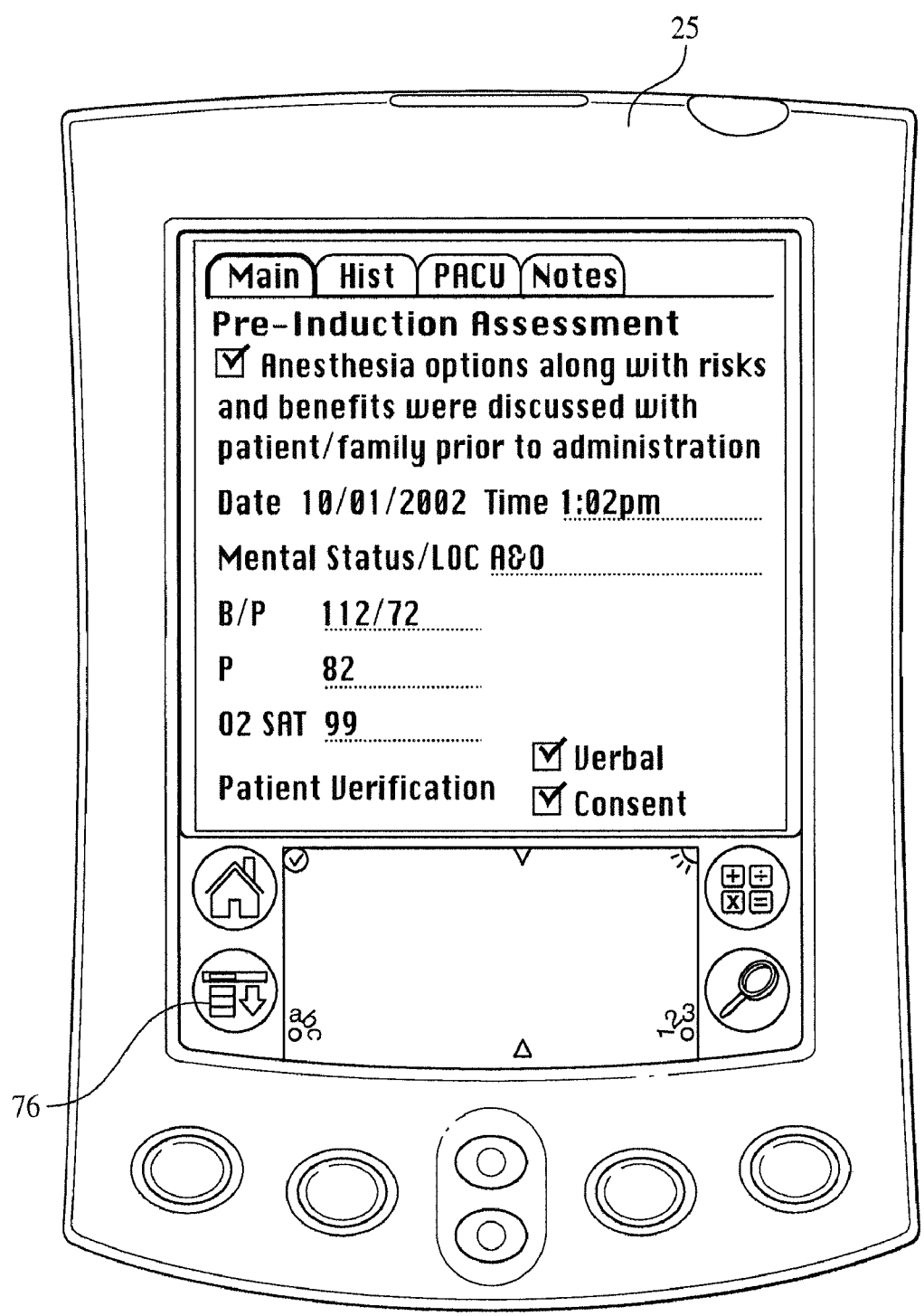
FIG. 11 is an exemplary Pre-Induction Assessment screen.

As a last step before administering the anesthetic, the anesthesia provider preferably navigates to the "Pre-Induction Assessment" screen (see, FIG. 11) by tapping the Menu icon 76 on the handheld display and then selecting Display/Pre-Induction Assessment from the drop-down menu. The Pre-Induction Assessment page needs to be completed before the anesthesia can begin. This form electronically ensures that the options and risks associated with the anesthesia procedure were explained to the patient and/or the patient's family before the procedure is commenced. Proper documentation of this disclosure is important to address any potential problems raised in the future.

Figure 12:
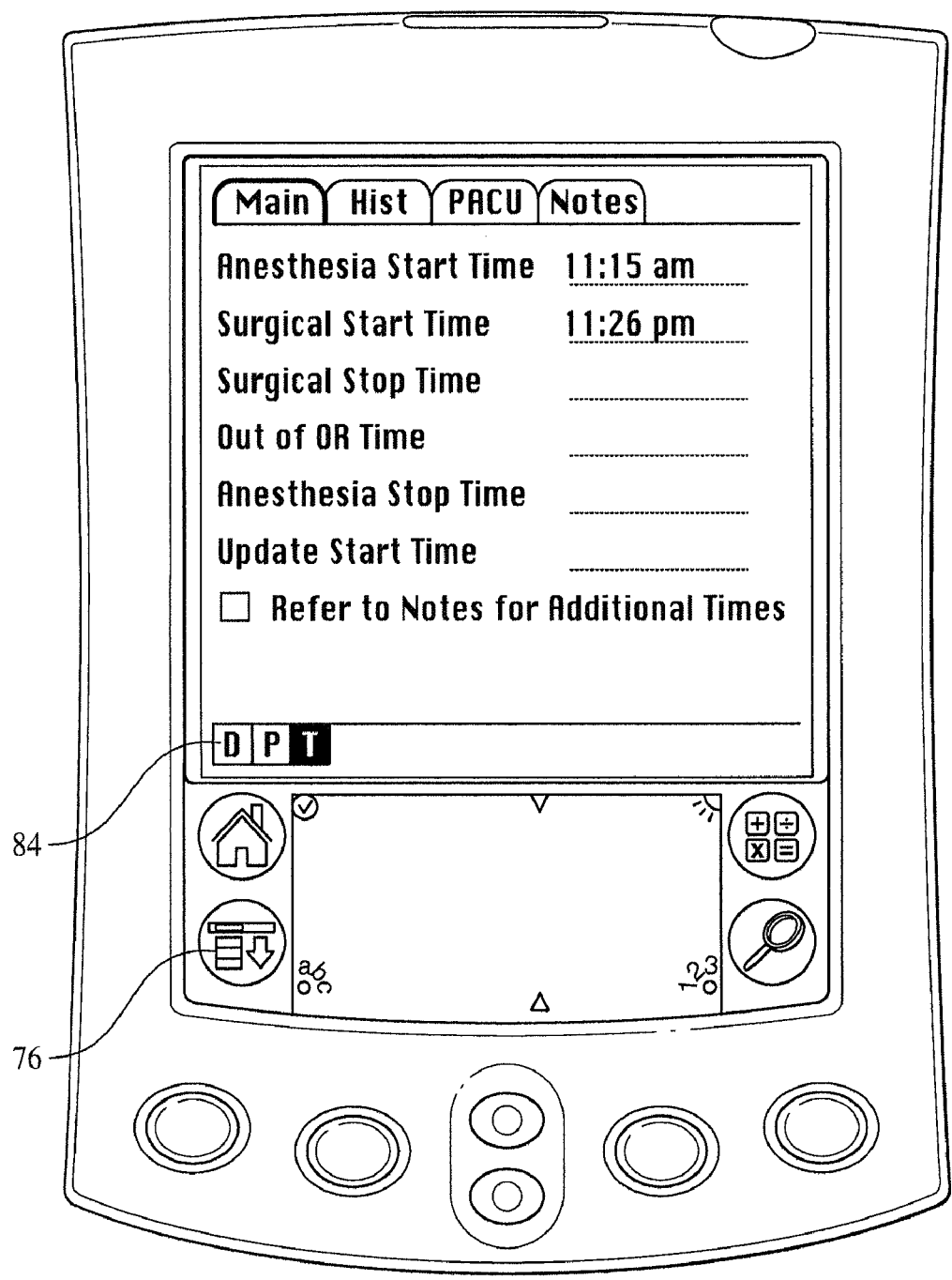
FIG. 12 is an exemplary procedure Timing screen.

When the surgical procedure is ready to begin, the anesthesia administrator preferably accesses the "Times" screen to note the procedure start time (see, FIG. 12). The Times screen may be accessed by either tapping the small square 84 with the letter "T" in it located on the bottom left-hand side of the screen or by tapping the Menu icon 76 on the handheld and selecting Display/Times from the pull-down menu. As shown in FIG. 12, the Times page includes space to record various timing information related to the procedure, the anesthesia process, and time spent in the OR. To begin the procedure, the "Anesthesia Start Time" line should be tapped and the present time will pop up. Tapping "OK" will then mark the present time as the official start time of the anesthesia record. An alternate time can also be entered in an intuitive manner.

Typically, once the procedure starts, the anesthesia provider will return to the Dosage Grid (see, FIG. 9), which is the area that medications, dosages, and different items that will be monitored such as EKG, $O_2$ saturation, $CO_2$, $O_2$%, temperature, and muscle relaxation using train-of-four will be recorded. FIG. 9 shows these fields partially filled out. To add a new drug to be monitored, tap one of the blank boxes 90 along the left-hand side of the screen and an "Enter Label" box appears. In the Enter Label box, a drop-down list of medications are listed, and a drop-down list of the way the anesthesia provider wants that particular medication measured will also appear. Tap what is needed and tap "OK" to enter one of the pre-entered medications. The anesthesia provider may also choose to manually enter a drug that is not listed, if desired, using the pop-up stylus keyboard. There are numerous blank boxes 90 that can be used depending on the procedure being performed, and the vertical scroll bar 92 may be used to page up and down the screen to reach other areas of the grid. At the bottom of the grid, the EKG, $O_2$ saturation, $CO_2$, $O_2$%, temperature, and muscle relaxation using the train-of-four have been pre-entered and can be filled out immediately. As a default, the information for this screen may be entered at five-minute intervals, and the graph can go up to twelve hours in length. There is also a horizontal scroll bar to move the graph to a different time period.

As briefly described above, the Dosage Grid includes a series of tabs along the top of the grid for navigating to other areas such as "History", "PACU", or "Notes". Along the bottom left hand corner of the Dosage Grid are three small squares 84 with the letters, "D", "P", and "T" which stand for Dosage Grid, Blood Pressure Grid, and Times, respectively. Tapping any of these squares will take the anesthesia provider directly to those screens. Further, the graph on the screen can automatically move along with time, which is called "Table Auto Shift". This feature can be activated in the "Preferences" screen, access to which is described below.

Figure 13:
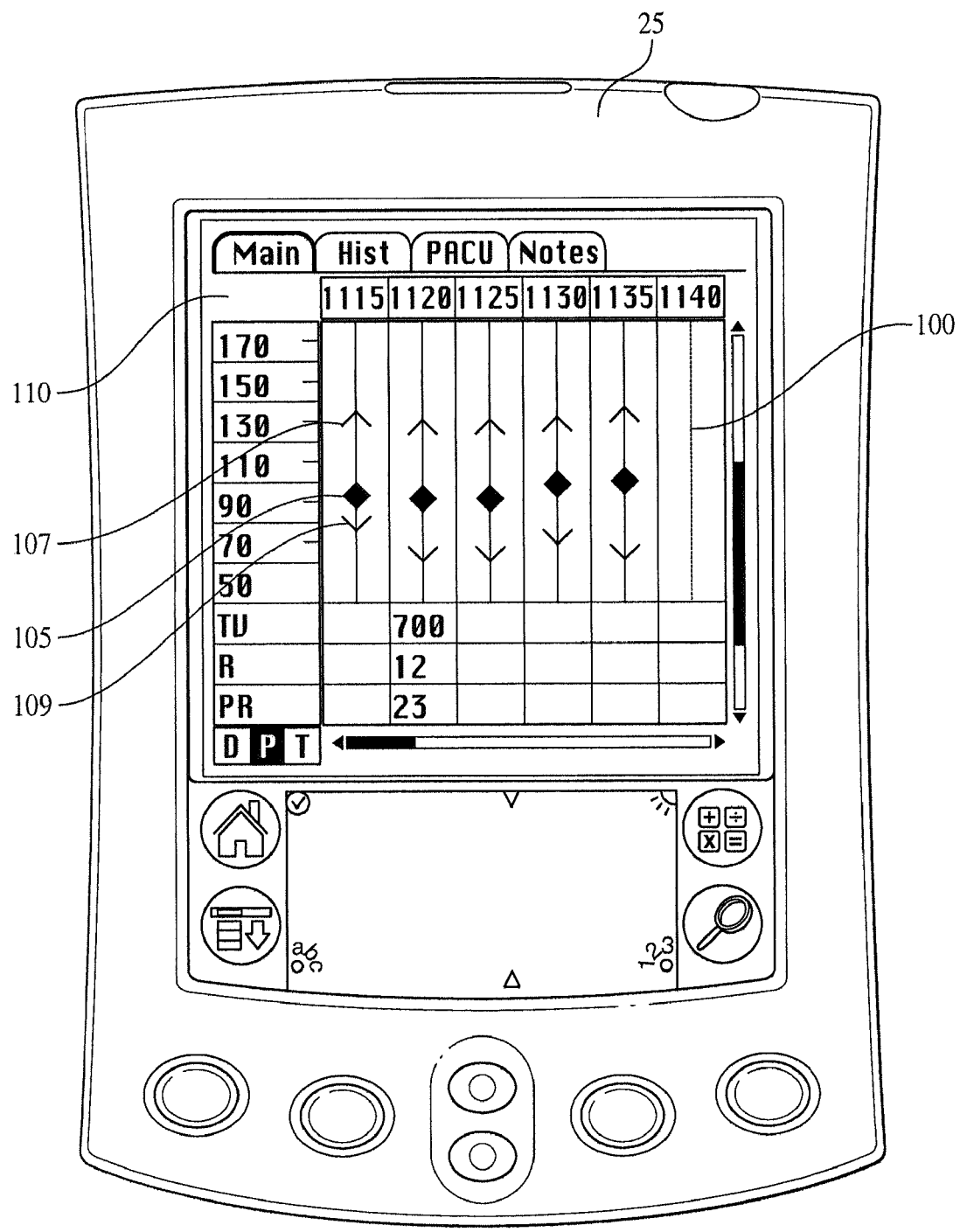
FIG. 13 is an exemplary Blood Pressure screen.

The next area that the anesthesia provider will typically go to is the Blood Pressure Grid (see, FIG. 13). As described above, this screen can be accessed by either selecting the "P" box with the stylus or tapping the Menu icon on the handheld device 25 with the stylus and then selecting Display/Blood Pressure Grid from the drop-down menu. The blood pressures can be quickly recorded in graphical fashion along with respiratory monitoring such as tidal volume, rate per minute, and inspiratory pressures through the use of this chart. To enter a blood pressure, the provider taps the dotted vertical line 100 (indicating a specific time period) with the stylus. A dot 105 and two angles 107, 109 will appear. By touching and holding either the dot 105 or one of the angles 107, 109, each can be individually moved up and down the vertical axis. The "dot" 105 represents the pulse, the upper angle 107 represents the systolic blood pressure, and the lower angle 109 represents the diastolic blood pressure. While moving the dot 105 and/or angles 107, 109, a numerical value 110 will appear in the upper left hand corner to indicate the numerical value of the pressure or pulse that is currently being changed with the stylus. When completed, the dotted line 100 becomes a solid line to indicate vital signs have been entered at that time. However, these values can be changed if an incorrect value was entered.

The anesthesia provider can also tap a specific time listed on top of the screen and a "Pulse & Pressure" window appears. Here the anesthesia provider can directly enter values or change the values to record the pulse and blood pressures. This may aid the user in entering an exact blood pressure or pulse rate for accuracy. Tapping "OK" if using this feature will enter the values in the blood pressure grid.

At some point in time during the procedure, the anesthesia provider preferably fills out the Intubation & Checklist records in the software system. These pages may be accessed by tapping the Menu icon 76 on the handheld 25 and selecting Display/Intubation & Checklist from the drop-down menu. These screens typically request information related to verification of the operation site, verification of consents and patient identification, airway management verification, positioning of the patient, NPO status, equipment used on the patient, equipment checked prior to use, choice of anesthesia, airway classification, ASA class, and IVs used. These screens are used to verify that the patient is cared for safely and diligently. Again, there are drop-down lists and the appropriate keyboards will pop-up when necessary.

A Supply Charges Screen may also be accessible using the Display drop-down menu. The Supply Charges screen allow the anesthesia provider to keep track of general hospital supplies (e.g., masks, tubing, syringes, etc.) that are used during the anesthesia procedure. These common items are often overlooked in a busy operating room, and this intuitive and quick selection screen will facilitate the hospital correctly charging for all supplies used during the procedure.

After the Intubation & Checklist and/or Supply Charges records are completed, or as necessary during the procedure, the anesthesia provider preferably returns to the Times screen (FIG. 12) to enter appropriate times as indicated such as the surgery start time, the surgery stop time, time when leaving the operating suite, and time when anesthesia care is completed. The anesthesia provider will mainly toggle back and forth between the Dosage Grid (FIG. 9) and the Blood Pressure Grid (FIG. 13) for the duration of the surgical procedure. During the surgical procedure, the remaining sections of Notes can also be completed (which include general information describing the hospital and personnel related to the procedure).

Figure 14:
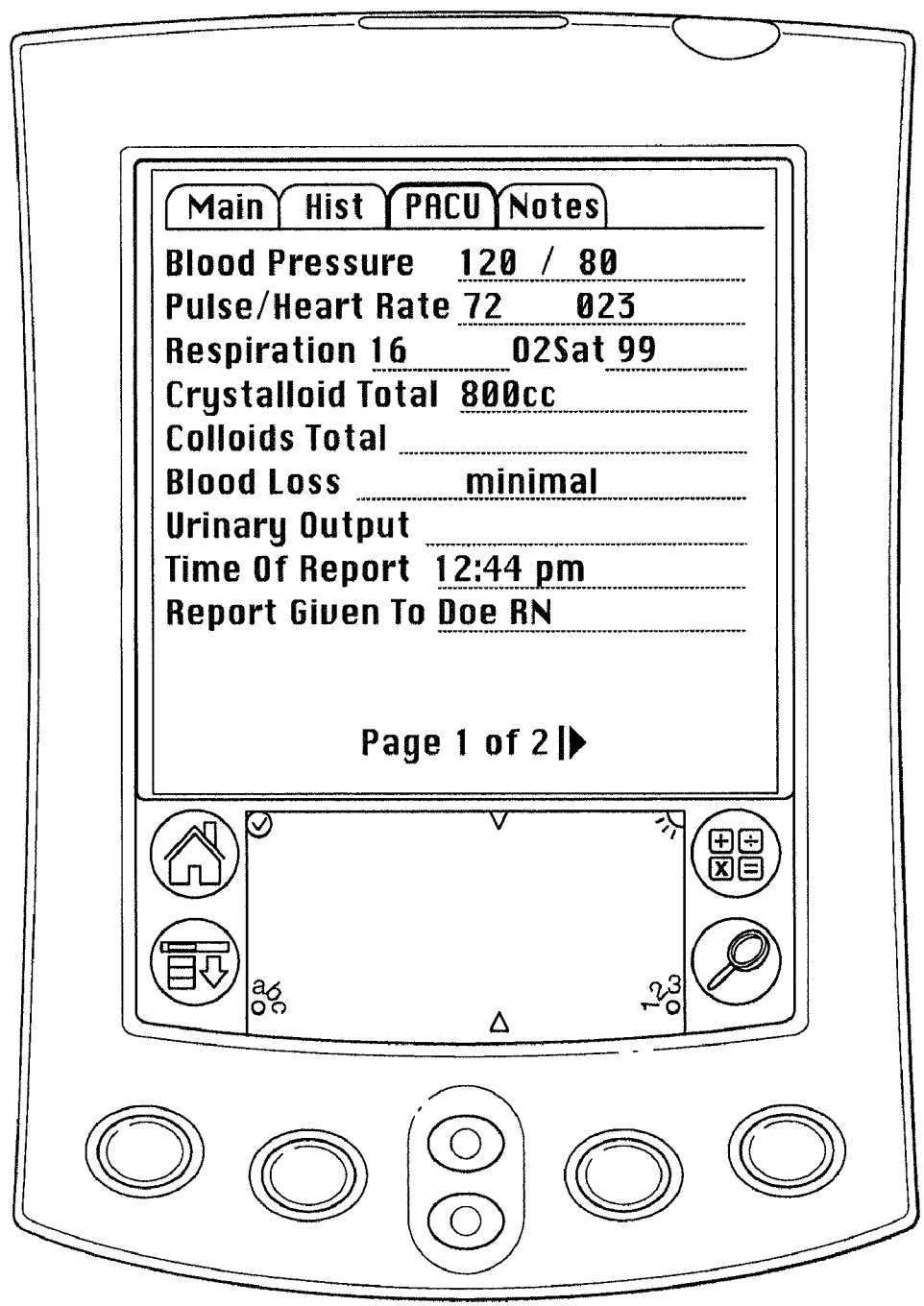
FIG. 14 is an exemplary PACU screen.

This information gathering process preferably proceeds until the end of the surgical procedure. At this time, the anesthesia provider has completed the case, and the patient is now in the post anesthesia care unit (PACU). To access the PACU pages (see, FIG. 14), the anesthesia provider need only tap the "PACU" tab from the Dosage Grid screen. On the first PACU screen (FIG. 14), the appropriate information is entered upon arrival to the PACU. Total amounts of various intravenous fluids are entered here along with the total amount of blood loss or urine that occurred during the procedure. The time of the report and to whom the report was given is also entered on this page. On the second page, a discharge note is written on the patient's status when the patient is being transferred out of the PACU. Again, the appropriate keyboards will automatically pop-up, when necessary.

Figure 15:
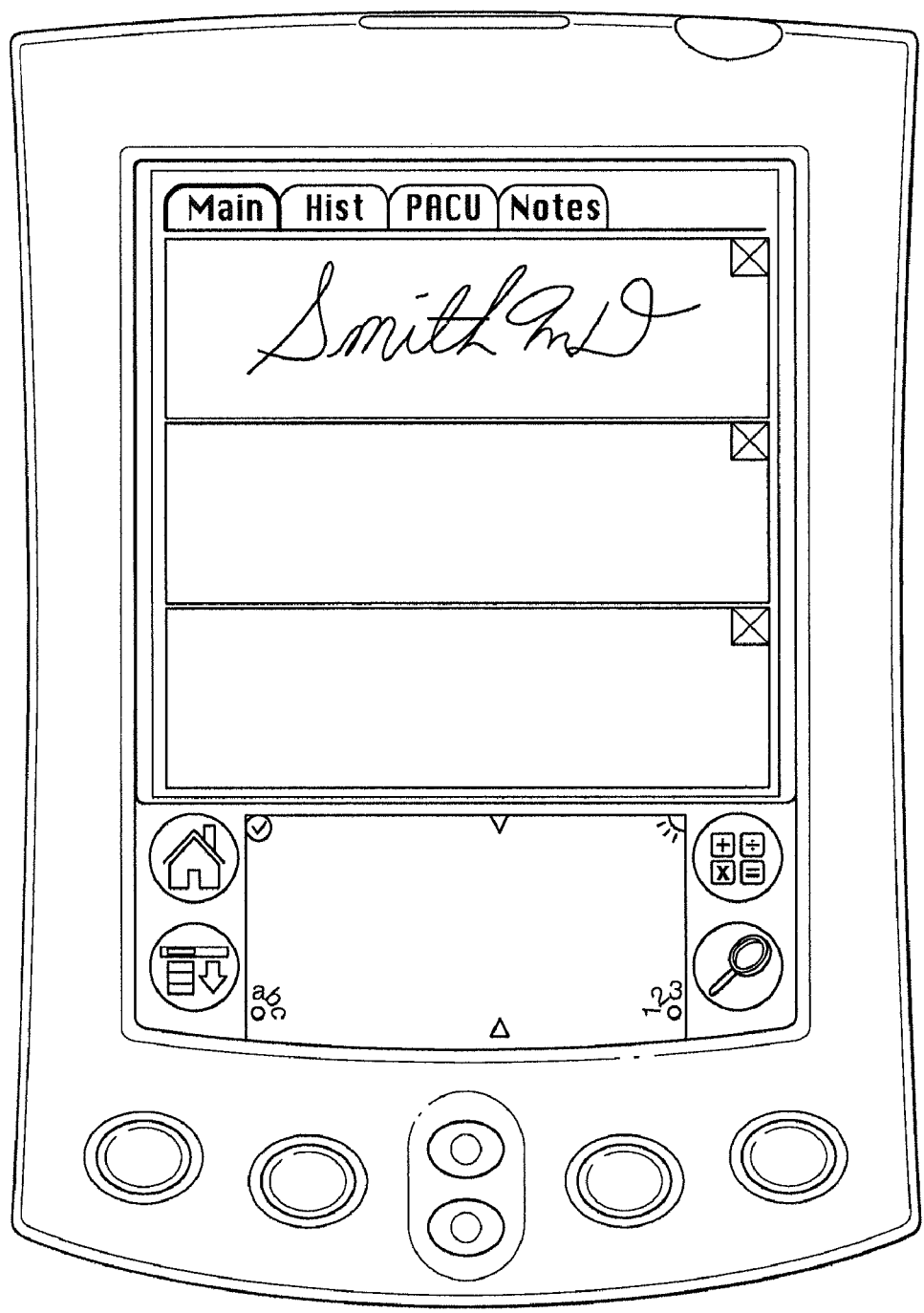
FIG. 15 is an exemplary Signature screen.

To complete the process, the anesthesia provider will complete the "Quality Assurance" record pages and electronically sign the handheld device 25 using the stylus (see, FIG. 15). These pages can be accessed by tapping on the Menu icon 76 on the handheld device 25 and selecting Display/Quality Assurance and Display/Signature from the drop-down menus. The quality assurance pages provide an important tool to analyze the overall care that is provided by the anesthesia department. For example, if an increased number of lip traumas during intubation were recorded, this increase will be assessed to find if there needs to be an in-service on intubation to demonstrate the proper technique. Trends can be identified and modified by using a quality assurance database. This will monitor and improve the level of care.

The signature page (FIG. 15) is used to electronically record a signature on the record to make the subsequently printed forms totally complete. If the anesthesia provider doesn't sign electronically, the stored records are not considered complete. An example of time saving using the electronic signature occurs if the pharmacy drug charge form is networked to the pharmacy computer, and the anesthesia provider's signature is already on the form. Otherwise the form needs to be printed out and signed and then sent on to the pharmacy. The electronic signature decreases the time spent processing the patient.

Once the complete anesthesia procedure information has been entered into the handheld device 25, this information needs to be synchronized into the main computer 15 that stores the patient information, and appropriate forms need to be printed out. To synchronize the data, the anesthesia provider should close out of the handheld software application, and place the handheld 25 in one of the available synchronization cradles 30 connected to main computer 15. The software program should then be opened on the main computer 15 (if not already running). Typically, the "Patient Information" screen will be present upon opening.

To begin the synchronization process, the anesthesia provider need only press the synchronization button (or other selector) on the handheld device cradle 30. The synchronization of information will occur between the handheld 25 and main computer 15. The anesthesia provider can search for a patient by the patient's medical record number, first name, last name, or date of birth and selecting the "Search" button. The application will then display one or multiple records that match the search criteria. If only one record matches the search criteria, that record will be displayed in the main Patient Information screen. If more than one record matches the search criteria, those records will be displayed in the list box window at the bottom of the Patient Information screen. The anesthesia provider can then select the record of choice.

To print a Patient Anesthesia Record, the user need only select "File/Print Records & Forms/Patient Record" from the pull-down menu. Likewise, there is a similar pull-down menu to print the Anesthesia Billing Form, the Pharmacy Drug Charges Form, and the Supply Charges Form.

The anesthesia provider or office staff can also enter information into the main computer 15 as well. This additional information is not entered on the handheld 25 as part of the procedure. The different additional information may include "Patient Information", "Contact Information", and "Procedure Information". Selecting the desired information button allows for the entry of the appropriate information. Preferably, information that comes from the handheld device 25 is placed in the Information windows and cannot be changed using the main computer 15.

Using the Quality Assurance (QA) on the main computer 15 can also be accessed using pull-down menus. The QA provides the capability for the anesthesia provider to perform queries on all quality assurance data. For example, queries may be run for a specified time period by selecting the appropriate button. Fixed Queries would be buttons such as "Today", "Yesterday", "Last 7 Days", and "Last 30 Days". Variable Queries would utilize buttons such as "Day" and "Period". To run a fixed query, the user selects the appropriate button and selects the appropriate procedure from the "Procedure" drop-down list. To run the Variable query, the user selects the appropriate button and selects the appropriate procedure from the "Procedure" drop-down list. The queries display the results of the query such as medical record number, first and last name, date of occurrence, and total the number of cases affected by the "Procedure". The results can then be printed as a quality assurance report.

There are at least four other areas on the main computer program, including: "Administration Panel"; "Patient Assignment"; "Patient Manager"; and "Settings". The Administration Panel allows the anesthesia provider to customize the list of surgeons and anesthesia staff on the handheld drop-down list of surgeons and anesthesia staff.

The Patient Assignment window can be displayed by selecting "Edit/Patient Assignment" from the pull-down menu. Once the patient's information is synchronized to the main computer 15, the information is placed in the database as an original record. The patient cannot be deleted from the database. Since the patient cannot be deleted from the "Patient to be Assigned" list, there is a choice of moving the patient's name to the Patient Manager list. To accomplish this move, the user selects a patient's name and selects "Hide". The patient is removed from the "Patient to be Assigned" list but is kept in the Manager list for storage. To assign a patient to a handheld 25, the user selects the patient's name and selects "Assign". The next time the anesthesia provider performs a synchronization procedure, the patient's information will be automatically transferred to the handheld 25. The anesthesia provider can remove a patient from the Assigned Patient list if a synchronization did not occur yet.

If multiple patient data storage locations are available, the anesthesia provider may change where the records are stored using a Setting menu. This provides the capability to choose where to store the patient reports.

The system software may optionally include additional features that provide added flexibility to the system. For example, there may be a "Preferences" screen on the handheld which includes general preferences such as "Auto PopUp Keyboard" (when the anesthesia provider taps a line to enter information, a keyboard pops up), "Recalculate Patient Weight", "Table Auto Shift" (moves the record graph along with present time), "Sound when table shifts" (when the graph moves in five minute intervals, a sound will occur), and "Auto Off" (the anesthesia provider can choose the "time on" feature of the handheld 25 on how long the handheld 25 will stay powered on before shutting off). The visual preferences may allow the graph to have a "Gray Grid Lines" appearance or the standard appearance.

Further, on graphical displays such as the Dosage Grid, there may be a bold vertical line located between the drugs listed and the graph. By tapping and holding down the stylus, the line may be dragged left and right to increase or decrease the size of the drug square. This feature customizes the displayed graph.

Additionally, in order to not over-write a patient with lesser information and erase important information, the software is preferably programmed such that the patient information can only go in one direction in a given situation. Specifically, if the patient record is created on the handheld 25, when the anesthesia provider performs a synchronization process, the patient's information is taken from the handheld 25 and placed on the main computer 15. That patient is no longer on the handheld 25. Likewise, when the anesthesia provider selects a patient on the main computer 15 and performs a synchronization process, that patient is locked on the main computer 15 so that no one else can transfer that patient's record from the main computer 15 to another handheld 25 until the original patient information is synchronized back from the handheld 25.

To aid in portability all of the information on the main computer 15 is stored in a common database format, such as MICROSOFT ACCESS, before any forms are printed. The database keeps the original information. A patient record cannot be deleted from the database. When a form is printed, the information is made into a MICROSOFT WORD or MICROSOFT EXCEL file (as common examples). The anesthesia provider may change the original information in the database since the data is date stamped. If there is a need to change or add or even delete information, the anesthesia provider selects a patient on the main computer 15 and performs a synchronization process. Then the change is made and performs another synchronization. Once the date has changed, the data cannot be changed.

Finally, the anesthesia provider can delete a patient record on the handheld 25 device. By selecting the program icon on the handheld 25, a Patient List appears. Selecting the desired patient's name and "Delete" will delete the patient from the handheld 25 device. If a patient is deleted before synchronization to the main computer 15, any information on the handheld 25 will be permanently deleted. Also, that patient will be permanently "locked" on the main computer 15 and can't be synchronized to another handheld 25.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. An anesthesia record data management system, comprising:
    a handheld computer device that includes manual input capability, digital input capability, and a display screen, wherein said handheld computer is capable of two-way communication with a main computer, wherein said at least one handheld computer device is capable of accepting data wherein said data is selected from the group consisting of patient information, drug information, and medical procedure information;
    further wherein said handheld device includes:
        a medical history module that includes a series of questions about the medical history of said patient in electronic format, where the manual input capability may be used to answer said series of questions;
        a notes module, wherein said notes module that displays pre-anesthesia information including an anesthesia care plan, regional anesthetic plan, monitors, invasive monitors, intubation, post-anesthesia care plan, analgesia program, and physical exam;
        a pre-induction assessment module that includes information about anesthesia options and risks and benefits discussed with said patient or family of said patient prior to administration of anesthesia;
        a timing information module that includes timing information related to a medical procedure being performed on said patient, an anesthesia process being performed on said patient, and an amount of time spent in surgery by said patient;
        a dosage display module that displays said drug information and said patient information in graphical format, wherein said drug information and patient information includes medications that are administered to said patient, dosages of said medications, and physiological measures that will be monitored during said procedure selected from the group consisting of EKG, $O_2$ saturation, $CO_2$, $O_2$%, temperature, and muscle relaxation;
        a blood pressure display module that displays blood pressure of said patient in real time and in graphical format, wherein said blood pressure display module coordinates with said dosage display module to display said blood pressure and said drug information in real time, wherein said dosage display module and said blood pressure display module integrate said blood pressure information and at least one physiological measure into a single display;
        an intubation and checklist module that includes information about the type of intubation performed, the quality of said intubation, the equipment used in said intubation, and patient consent data; and a main computer with an information record database, wherein said main computer generates an anesthesia record, an anesthesia billing form, a pharmacy medication charge form, and an anesthesia quality assurance report using data from said modules.

2. The data management system of claim 1, wherein said medical procedure information includes a surgical procedure performed on a patient, a start time for said surgical procedure, and a duration of said surgical procedure.

3. The data management system of claim 1, wherein said physiological measures are provided to said handheld computer device from hospital monitors via said digital input capability.

4. The data management system of claim 3, wherein said patient information is updated in real time.

5. The data management system of claim 1, wherein said patient information is entered into said handheld computer device by a medical professional using said manual input capability.

6. The data management system of claim 1, wherein said patient information is communicated from said handheld computer device to said main computer in real time.

7. The data management system of claim 1, wherein said handheld computer device is capable of collecting data from more than one patient simultaneously.

8. The data management system of claim 1, wherein said handheld computer device is capable of downloading said medical history from said main computer.

9. The data management system of claim 1, wherein said handheld computer device is capable of receiving a signature from a medical practitioner via said manual input capability.

10. The data management system of claim 1, wherein said drug information relates to multiple surgical procedures.

11. The data management system of claim 1, further comprising at least one docking cradle that allows for a synchronization process between said handheld computer device and said main computer.

12. The data management system of claim 1, wherein the handheld computer device is capable of generating reports.

13. The data management system of claim 1, wherein said main computer is communicatively connected to a computer local area network which includes a pharmacy computer.

14. The data management system of claim 1, wherein said main computer is communicatively connected to a remote computer system, wherein said remote computer system includes an insurance company computer network, a pharmacy, or a medical supplies provider.

15. The data management system of claim 1, wherein said reports are selected from the group consisting of an anesthesia record, an anesthesia billing form, a supply charges form, a pharmacy charge form, and a quality assurance report.

16. The data management system of claim 1, further comprising a supply charges module that is adapted to accept information via said manual input capability or said digital input capability about medical supplies that are used during said medical procedure.

17. The data management system of claim 1, wherein said handheld further comprises:
    a post-anesthesia care unit module that is adapted to accept post-medical procedure information about said patient vital signs, total fluids infused, and total colloids and crystalloids, and time the report was given, further wherein said post-anesthesia care unit module is adapted to generate a discharge summary; and
    a quality assurance module that is adapted to allow a medical professional to digitally sign electronic forms relating to a quality of care of said patient.

18. The data management system of claim 17, wherein said anesthesia billing form is generated using at least said timing information and said dosage information.

19. A method for managing patient data in an anesthesia record-keeping system utilizing at least one handheld computer device and a main computer, comprising the steps of:
- displaying notes on pre-anesthesia information on said handheld device, wherein anesthesia information includes an anesthesia care plan, regional anesthetic plan, monitors, invasive monitors, intubation procedures, post-anesthetic care plan, analgesia program, and physical examination;
- displaying information on said handheld device about pre-induction assessment that includes anesthesia options and risks and benefits discussed with said patient prior to administration of anesthesia;
- obtaining dosage information including medications that are administered to a patient, dosages of said medications, and physiological measures that are monitored during said procedure selected from the group consisting of EKG, $O_2$ saturation, $CO_2$, $O_2$%, temperature, and muscle relaxation;
- displaying timing information related to a medical procedure being performed on said patient, an anesthesia process being performed on said patient, and an amount of time spent in surgery by said patient on said handheld device;
- displaying said dosage information on said handheld device in real time and graphical format;
- displaying blood pressure of said patient on said handheld device in real time and in graphical format, wherein said blood pressure information and at least one of said physiological measures are combined into a single display;
- displaying information on said handheld device about intubation; including information about the type of intubation performed, the quality of said intubation, and the equipment used in said intubation, and patient consent data on said handheld device;
- synchronizing the handheld computer device to the main computer, wherein said synchronizing occurs in real time; and
- generating documents with said main computer using data from said handheld device, wherein said documents include anesthesia record, anesthesia billing form, pharmacy medication charge form, and anesthesia quality assurance report.

20. The method of claim 19, wherein said step of obtaining medical history information occurs by transmitting pre-stored patient information from the main computer to the handheld computer device.

21. The method of claim 20, wherein said anesthesia quality assurance report is generated based on at least said post-anesthesia care procedures.

22. The method of claim 19, wherein said handheld computer device and said main computer are communicatively connected using at least one handheld computer device cradle or a wireless connection.

23. The method of claim 19, further comprising displaying information about supply charges by the main computer, including information about medical supplies that are used during said medical procedure.

24. The method of claim 19, further comprising entering information about post-anesthesia care procedures including information about said patient vital signs, total fluids infused, and total colloids and crystalloids, and time the report was given.

25. The method of claim 19, further comprising digitally signing electronic forms of said generated documents.

26. The method of claim 25, wherein generating said pharmacy medication charge form includes using at least said dosage information, said timing information, and said digitally signed electronic forms.

27. The method of claim 25, wherein generating said anesthesia billing form includes using at least said timing information and said dosage information.

28. The method of claim 19, wherein said physiological measures are obtained from a medical monitor.

* * * * *